United States Patent
Guracar et al.

(10) Patent No.: US 7,775,981 B1
(45) Date of Patent: Aug. 17, 2010

(54) CONTRAST IMAGING BEAM SEQUENCES FOR MEDICAL DIAGNOSTIC ULTRASOUND

(75) Inventors: Ismayil M. Guracar, Redwood City, CA (US); Patrick J. Phillips, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2509 days.

(21) Appl. No.: 09/657,635

(22) Filed: Sep. 6, 2000

(51) Int. Cl.
*A61B 8/00* (2006.01)

(52) U.S. Cl. .................................. 600/447; 600/458

(58) Field of Classification Search ............... 600/437, 600/439, 441–447, 458; 73/625–628; 367/103–105, 367/138
See application file for complete search history.

(56) References Cited

U.S. PATENT DOCUMENTS

| 5,632,277 A | 5/1997 | Chapman et al. |
| 5,675,554 A | 10/1997 | Cole et al. |
| 5,951,478 A | 9/1999 | Hwang et al. |
| 6,095,980 A | 8/2000 | Burns et al. |

OTHER PUBLICATIONS

Johan Kirkhorn et al., Improved Ultrasound Contrast Detection Combining Harmonic Power Doppler with a Release-Burst; 1999 IEEE Ultrasonics Symposium; pp. 1697-1700.

*Primary Examiner*—Francis Jaworski

(57) ABSTRACT

A transmit sequence for contrast agent imaging that improves sensitivity and minimizes image artifacts. The number of pulses and the interleaving of spatially distinct pulses between spatially co-linear pulses are selected such that a substantially similar pulse sequence for substantially each line in a scanned region is generated. A collateral pulse from a different scan line is interleaved between at least two imaging pulses along a scan line of interest. Such pulse sequences provide sensitive contrast agent imaging with minimized spatial variation. In another aspect, responsive signals representing the first and second scan lines are obtained. Intensities associated with the signals are determined. The intensities associated with the first scan line are compared to a value. The signals associated with the first scan line are replaced by the signals associated with the second scan line, signals associated with the first and second scan lines, or neighboring signals in time or space as a function of the comparison. Thus, signals associated with an image artifact may be replaced by signals along other scan lines so good spatial resolution is maintained.

37 Claims, 5 Drawing Sheets

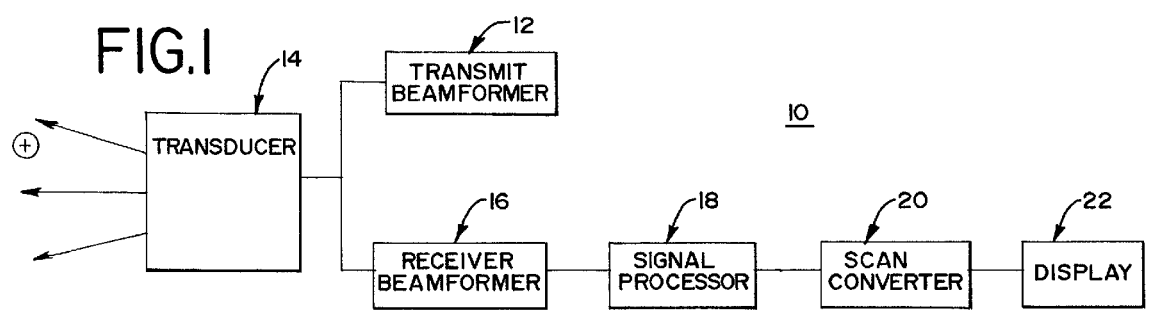
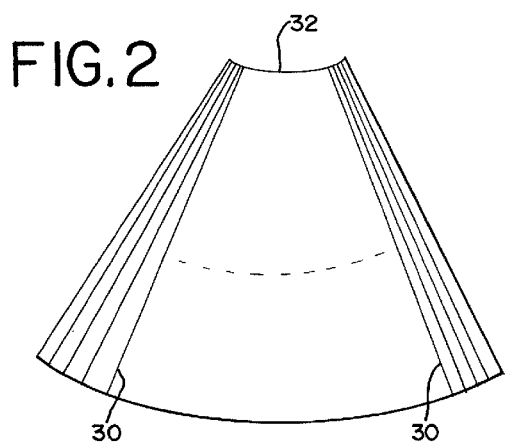

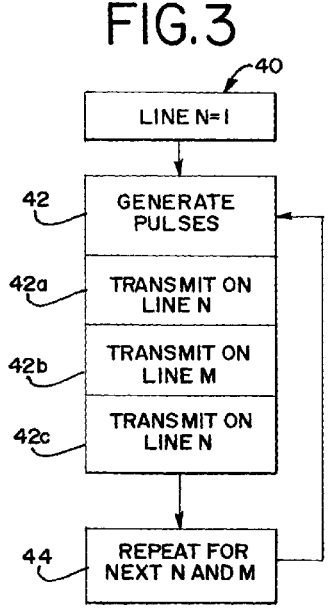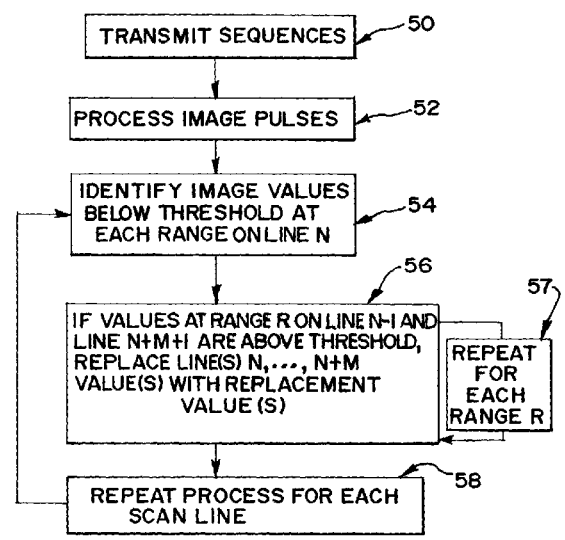

```
           LINE NUMBER
TIME        1 2 3 4 5
  0         e C e
              e C e
 PRI        e C e
              e C e
 2PRI       e C e e C e
                e C e
              e C e
                e C e
              e C e e C e
                    e C e
                  e C e
                    e C e
                  e C e
```

CONTRAST IMAGING BEAM SEQUENCES FOR MEDICAL DIAGNOSTIC ULTRASOUND

BACKGROUND

This invention relates to contrast agent imaging beam sequences for a medical diagnostic ultrasound system. In particular, transmit and associated receive sequences are provided.

Contrast agents, such as microspheres, are added into a patient to assist in medical diagnostic imaging. Contrast agents are sensitive to acoustic energies. Transmissions of acoustic energy destroy or modify contrast agent. A loss of correlation due to changes of the contrast agent is determined and used to generate a medical diagnostic ultrasound image. In another method of detection, movement of the contrast agent without loss of correlation or in combination with some loss of correlation may be used to generate ultrasound images.

To determine the loss of correlation or movement of contrast agent, multiple beams of acoustic energy along the same lines or to the same locations are transmitted. Resulting echoes from the transmissions are sampled for determining the loss of correlation.

Various transmit and associated energy sequences for loss of correlation or motion detection imaging have been used. For example, a flow sample interleave ratio (FSIR) of one and a flow sample count (FSC) of three are used. As a result, three transmissions for three pulse repetition intervals are fired along each scan line before firing along the next or adjacent line. For each scan line except the edge scan lines for a region of an image, a pulse or energy sequence of e e e C C C e e e is provided, where e represents energy from a transmit pulse along a different scan line (e.g., such as an adjacent scan line) and C represents energy from the transmit pulse along the transmit line of interest. Energy from transmit pulses along adjacent scan lines acts to destroy the contrast agent before the transmissions used for detecting movement or loss of correlation sampling are fired.

Other sampling sequences have been used for motion detection or loss of correlation imaging. For example, a FSIR of two with a FSC of three provides pulse or energy sequences that alternate or differ across alternative scan lines. FIG. 5E represents this example. Imaging pulses are labeled "C" and are associated with displayed scan lines 1 through 5. Collateral energy pulses on one scan line that are from transmissions on neighboring scan lines are labeled "e". For odd scan lines and ignoring the first scan line in an image, scan line one, the energy sequence comprises e e e CeCeCe, and for even scan lines the energy sequence comprises eCeCeC e e e. For odd number scan lines, a greater amount of bubble destruction before detection sampling is provided than for even scan lines. A FSIR of three with a FSC of three also results in differing energy sequencing as a function of scan line. The different amount of collateral destruction for different scan lines may cause a loss in sensitivity and visual artifacts. While the FSIR=1 sequence minimizes artifacts, poor sensitivity is provided due to the amount of destruction before the imaging pulses.

In another contrast agent imaging technique, one or more transmit pulses designed for destroying contrast agents without associated receive sampling are transmitted. For example, a FSIR=1 with a FSC=3 is used such that a destruction pulse is transmitted between the first two imaging pulses of the flow sample count. Substantially each transmit line is associated with an energy sequence of ede e CDC C ede e, where d is the collateral energy from destruction transmission along adjacent scan lines and D is the destruction transmit pulse along the scan line of interest. Like the other examples above, poor sensitivity is provided due to the amount of destruction prior to an imaging transmit pulse.

BRIEF SUMMARY

The present invention is defined by the following claims, and nothing in this section should be taken as a limitation on those claims. By way of introduction, the preferred embodiments described below include a method and system for transmitting sequences of acoustic energy. The number of pulses and the interleaving of spatially distinct pulses between spatially colinear pulses are selected such that a substantially similar pulse sequence for substantially each line in a scanned region is generated. A collateral pulse from a different scan line is interleaved between at least two imaging pulses along a scan line of interest. Such pulse sequences provide sensitive contrast agent imaging with minimized spatial variation.

In a first aspect, a substantially similar energy sequence is provided for substantially each scan line in a region. The energy sequence includes at least one collateral energy pulse between two imaging pulses.

In a second aspect, a first pulse is transmitted along a first scan line. Afterwards, a second pulse is transmitted along a second scan line that is adjacent to the first scan line. A third pulse is then transmitted along the first scan line. This transmission sequence is repeated such that a substantially same sequence of pulses is provided for each of a plurality of scan lines.

In a third aspect, pulses are transmitted with a flow sample interleave ratio greater than 1. A substantially similar energy sequence for substantially each line in a scanned region is generated. Energy responsive to each transmitted pulse is then sampled.

In a fourth aspect, a different technique for imaging contrast agents is provided. Acoustic energy is transmitted along first and second scan lines in a target that includes contrast agents. Responsive signals representing the first and second scan lines are obtained. Intensities associated with the signals are determined. The intensities associated with the first scan line are compared to a value. The signals associated with the first scan line are replaced by the signals associated with the second scan line, the first and second scan lines or neighboring signals in time or space as a function of the comparison. Thus, signals associated with an image artifact may be replaced by signals along other scan lines so good spatial resolution is maintained.

Further aspects and advantages of the invention are discussed below in conjunction with the preferred embodiments.

BRIEF DESCRIPTION OF SEVERAL VIEWS OF THE DRAWINGS

FIG. 1 is a block diagram of a medical diagnostic ultrasound system for contrast agent imaging of one embodiment.

FIG. 2 is a graphical representation of one embodiment of a scan line format.

FIG. 3 is a flow chart representing one embodiment of a transmit pulse sequence.

FIG. 4 is a flow chart diagram representing an embodiment of an image artifact replacement method.

FIGS. 5A-E are graphical representations of transmit pulse sequences and associated collateral energy.

DETAILED DESCRIPTION OF THE PREFERRED EMBODIMENTS

Figure 6:
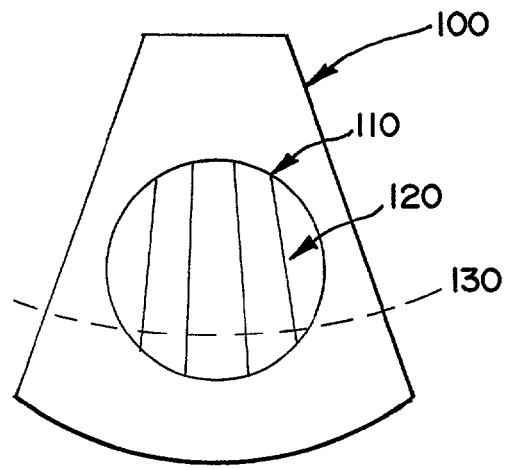
FIG. 6 is a graphical representation of an image with lines of reduced sensitivity.

The preferred embodiments discussed below provide sensitive contrast agent imaging with minimum line-to-line spatial variation. In one embodiment, signals associated with image artifacts are replaced with signals from adjacent scan lines. In another embodiment, substantially similar pulse sequences are generated for each line in a region. The sequences are generated by properly interleaving imaging pulses along adjacent scan lines with imaging pulses along the scan line of interest to minimize collateral destruction from imaging pulses along neighboring scan lines.

FIG. 1 shows a block diagram of a medical diagnostic ultrasound system 10 for contrast agent imaging. For example, a Sequoia®, Aspen™, or 128XP® ultrasound system manufactured by Acuson Corporation may be used. Other ultrasound systems, such as systems provided by other manufacturers or remote workstations, may be used.

The system 10 includes a transmit beamformer 12, transducer 14, a receive beamformer 16, a signal processor 18, a scan converter 20 and a display 22. The transmit beamformer 12 comprises analog or digital circuitry for generating excitation waveforms. In one embodiment, the transmit beamformer 12 comprises a transmit beamformer disclosed in U.S. Pat. No. 5,675,554, the disclosure of which is incorporated herein by reference. Other transmit beamformers may be used, such as analog or memory based beamformers for generating unipolar, bipolar or sinusoidal modulated or unmodulated transmit waveforms.

The transducer 14 comprises a linear, curved linear one-dimensional, two-dimensional, 1.5 dimensional, annular or other array of transducer elements. In response to excitation waveforms, the transducer transmits acoustic energy into a region of a patient to be scanned. Acoustic echoes responsive to the acoustic energy are converted to electrical signals by the transducer 14.

The receive beamformer 16 comprises analog and/or digital circuitry for processing the electrical signals to represent the scanned region. In one embodiment, the receive beamformer 16 comprises a receive beamformer disclosed in U.S. Pat. No. 5,685,308, the disclosure of which is incorporated herein by reference. For motion detection and/or loss of correlation imaging, the receive beamformer 16 comprises digital circuitry, buffers or memories sufficient to allow FSIR of two or more with a FSC of two or more. For example, two banks of 128K byte memories are provided. Each bank of memory is operable to store data for 256 scan lines with a total of 512 range samples. For FSC=3, each bank holds 85 receive lines. If the range grid is reduced to a maximum of 256 range samples, 170 scan lines may be received and stored. Samples are stored in groupings in the same banks of memory. The banks are used in an interleaved manner to allow the processing of receive signals to keep pace with the acquisition. Other memory structures may be used, such as with more than two banks or dual part RAM.

The signal processor 18 comprises one or more general processors, digital signal processors, ASICs, analog circuits, or other digital circuits. In one embodiment, the signal processor includes a Doppler processor, but a B-mode processor may alternatively or additionally be included. The signal processor 18 detects contrast agent information from the receive beamformed signals. For example, the loss of correlation between two or more samples from a same location of a patient is detected. The Doppler processor determines a difference in energy between samples representing a same location at different times. The Doppler processor may include a clutter filter programmed to reduce signals that have a high degree of correlation, such as signals associated with tissue flash or vessel wall motion. In alternative embodiments, the B-mode detector is used.

Other processing may be performed in either a B-mode processor and/or a Doppler processor. For example, conventional color flow processing may be used. Energy, variance, and/or velocity signals may be detected and displayed. Other techniques such as Pulse Inversion (see U.S. Pat. Nos. 5,951,478, 5,951,478 and 5,632,277) or Pulse Inversion Doppler (see U.S. Pat. No. 6,095,980) with FSCs greater than two may be used. Contrast Pulse Sequences or detecting odd and even order scattering (see U.S. application Ser. No. 09/514,803) may also be used with the invention. All of these aforementioned techniques vary the amplitude and/or phase on transmit and/or receive between pulses within a FSC to improve contrast agent imaging. These methods of processing contrast agent signals are not limiting and other techniques may be used with the sequences disclosed herein.

The signal processor 18 may include filtering circuitry. For example, a spatial filter filters samples of detected intensities associated with different locations within the scanned region. The spatial filter coefficients are selected such that reduced sensitivity to variations in energy sequences across ultrasound lines is provided. For example, a spatial filter that varies coefficients as a function of scan line is provided. The number of samples used for each spatial filtering operation includes samples associated with successive transmissions, resulting in a large spatial filter. Alternatively, spatial filtering is performed after the loss of correlation or motion is detected.

The scan converter 20 comprises circuitry for converting data from a polar coordinate scan format into a Cartesian coordinate format for display. The display 22 comprises a monitor or other device for providing an ultrasound image responsive to the received echo signals. In one embodiment, the image comprises a loss of correlation or motion detection image of a region including contrast agents.

Image artifacts within the image on the display 22 may be minimized or controlled as a function of the transmit sequence. FIG. 2 is a graphical representation of a scan line format comprising a sector or Vector® format. A plurality of scan lines 30 from a sector shaped region 32 of an image. Except at the edges, each scan line 30 has two adjacent scan lines. Other scan formats may be used, such as linear formats.

The transmit beamformer 12 generates electrical excitation waveforms that are converted to acoustic energy by the transducer 14. The acoustic energy is focused along one or more of the scan lines 30. In one embodiment, a substantially similar energy sequence is provided for each transmit pulse along the scan lines 30. In alternative embodiments, different power levels may be used for transmit pulses along different scan lines. Other characteristics, such as frequency, amplitude, phase, aperture size, element spacing, apodization profile, focal point and/or beam width, may be the same or vary as a function of scan line. Receive beamformation characteristics may also be the same or differ as a function of scan line. The same characteristics may also be varied between different pulses along the scan line.

The transmit pulses are interleaved between scan lines 30. The interleaving is represented by the FSIR. For a FSIR=2, transmission along two scan lines 30 are performed alternatively or in an interleaved manner. The transmit pulses are also associated with a FSC. The FSC represents the number of transmissions along any given unique scan line 30. For example, a FSIR=2 with a FSC=3 is provided. Three temporally spaced transmit pulses are fired along each scan line and are interleaved between two adjacent scan lines. Using any given scan line 30 in this example, every other transmit pulse for a series of three total transmit pulses are fired along that scan line. The transmit pulses interleaved between the transmit pulses for that line are associated with one or both of the adjacent scan lines.

In response to the transmit pulse sequence, each scan line at any given depth is provided with a sequence of acoustic energy or pulses. The energy sequence is responsive to imaging pulses transmitted along the scan line of interest, and one or more adjacent scan lines or other scan lines. Energy from transmit pulses along a scan line 30 of interest comprises energy from imaging pulses. Energy along the scan line 30 from transmit pulses along adjacent scan lines comprises collateral energy. Using a FSIR greater than one interleaves pulses from adjacent scan lines and therefore interleaves collateral energy pulses with imaging energy pulses. Energy along a scan line of interest resulting from an adjacent scan line has a lesser amplitude than the energy associated with a transmit pulse along the scan line of interest where the imaging transmit pulses are transmitted with about the same power level.

The energy sequence along each scan line 30 is said to be "substantially" similar to allow for energy associated with transmit pulses along scan lines other than the scan line of interest and immediately adjacent scan lines. Scan lines 30 adjacent to or near the edge of the scan region 32 may comprise a different sequence as a function of the scan line position. Thus, as used herein, substantially each scan line having a similar energy sequence includes or allows for scan lines with a different sequence as a result of being near the edge of the scan region 32. Furthermore, some spatial variation as a function of scan lines 30 may be provided for other purposes.

FIG. 3 is a flow chart diagram representing one embodiment of a transmit sequence for imaging of contrast agents. In act 40, the scan line N is set equal to one. A scan line number one is associated with a left most or right most scan line within the region to be scanned. In alternative embodiments, the scan line number one is at any of various scan line positions within the region to be scanned.

In act 42, transmit pulses for receive sampling (i.e., imaging pulses) are generated. For example, act 42A represents transmitting a pulse along scan line N. In act 42B, a transmit pulse is generated along a different scan line M, such as an adjacent scan line (e.g., M=N-1 or N+1). In act 42C, another transmit pulse is fired along the transmit line N. Additional transmit pulses along scan line N or an adjacent scan line, such as scan line M, may be provided.

In act 44, one or both of scan lines N and M are incremented or decremented. For example, scan line M is incremented to be equal to N, and N is set equal to be M+1. Acts 42 and 44 are repeated to scan the entire region of interest. The scanning of the entire region of interest is sequenced as discussed above. Alternatively, a more randomized sequence may be provided for creating substantially similar energy sequences along a plurality of scan lines with minimized collateral destruction of contrast agents.

In one embodiment, the transmit sequence FSIR is greater than one. For example, an FSIR=2 with an FSC=3 sequence is used. The resulting energy or pulse sequence has a minimized amount of collateral destruction with the substantially same sensitivity or spatial distribution for substantially all the scan lines. The energy sequence comprises e eCeCeCe e. FIG. 5A shows this sequence for seven scan lines.

In another embodiment, a FSCR=3 with a FSC=4 is provided as shown in FIG. 5B. Substantially each scan line is provided with an energy sequence of e eC eCeeCe Ce e.

In the examples above, the FSIR is equal to an integer multiple of the FSC-1. In general, such a transmit pulse sequence and associated sampling sequence provides an optimal frame rate with increased sensitivity and minimization of image artifacts. The empty or null pulse repetition intervals without collateral energy or imaging transmit pulse energy shown in the sequences above as spaces allow a uniform sequence of energy along all scan lines.

In other embodiments, dummy samples or inserting a period of no transmissions may be used. For example, in a transmit pulse sequence of FSIR=3 with FSC=3, a null pulse (i.e., no pulse) is associated with one pulse repetition interval and is inserted within the sequence between every third transmit pulse. The resulting energy sequence comprises e eC eCe Ce e. FIG. 5C shows this transmit sequence.

In a further embodiment, transmit pulses for destroying contrast agents without receive sampling (destruction pulses) are transmitted. Destruction pulses are interleaved with imaging pulses to increase the loss of correlation effect and allow a lower power transmission for the imaging pulses. Destruction pulses may be associated with a high pulse repetition frequency since returned echoes are not sampled. Higher energy, different or varying frequency, lower frequency, longer pulse duration, pulses with spectral content tuned to the contrast agent and/or simultaneous transmission along different scan lines may be used for destruction pulses as compared to imaging pulses. Destruction pulses are further described in U.S. Pat. No. 6,340,348 (application Ser. No. 09/348,246, filed Jul. 2, 1999), the disclosure of which is incorporated herein by reference. Since destruction pulses are not used for imaging, the destruction pulses may be transmitted immediately after echoes responsive to the imaging transmit pulses have been received from the deepest depth of interest. The timing of the transmitted destruction pulses may vary and may be arranged to maximize the frame rate.

Destruction pulses are interleaved with the imaging pulses such that substantially each scan line is subjected to a similar energy sequence at any given depth. For example, a FSIR=2 with a FSC=4 sequence is used. Destruction pulses are interleaved once for every flow sample count sequence of four imaging pulses. For example, the destruction pulse is interleaved between the second and third imaging pulses of the flow sample count. FIG. 5D shows the transmit pulse sequence and associated collateral energy for an eight scan line example. Substantially each scan line is subjected to an energy sequence of e ede CeCDCeC ede e, where D is the energy associated with the destruction pulse along the scan line of interest and d is the collateral energy from a destruction pulse transmitted along an adjacent scan line. Additional destruction pulses may be used per scan line. In yet other alternative embodiment, null firings or no transmission at various points within the transmit pulse sequence are provided. Destruction pulses may also be used for B-mode imaging.

In alternative embodiments, the transmit pulse sequence and associated receive sampling sequence are interleaved between non-adjacent scan lines. Likewise, destruction pulse transmissions may be interleaved between non-adjacent scan lines. In yet other embodiments, the transmit sequence is arranged in a varying order not following FSIR and FSC characterization alone.

FIG. 4 shows an alternative or additional method for reducing image artifacts in contrast agent images while preserving spatial resolution. For example, where an ultrasound system architecture or hardware has limited memory or other capabilities so that the interleaving sequences discussed above may not be used or may be used in certain groups of scan lines of the image, the image artifact identification and replacement techniques discussed below may be used. Samples associated with image artifacts are replaced by samples along adjacent scan lines not associated with an image artifact. This method avoids unnecessary excessive spatial or temporal smoothing to minimize the artifacts.

In act 50, transmit pulses are fired along the scan lines. The transmit sequence used may be as discussed above or a different transmit sequence, such as discussed in the background section. Destruction pulses may also be transmitted. In act 52, echo signals are received and sampled in response to the various imaging transmit pulses. These signals are processed to extract the signal parameters of interest, such as intensity values. The intensities for the sampled signals are obtained, such as obtaining in-phase and quadrature data or data detected using B-mode or Doppler processes.

The intensities associated with one scan line, a sample, or groups of samples are compared to a threshold or other intensities in act 54. The threshold may be a user selected variable, an application specific variable, a variable programmed into the system or a variable adaptive to other signal information. The threshold is selected such that intensities above the threshold are associated with desired contrast agents signals due to loss of correlation and/or motion. Signals or intensities below the threshold are associated with image artifacts. In other embodiments, the intensities are compared to other intensities, such as intensities from adjacent samples or an average of another group of intensities (e.g., an average of intensities along an adjacent scan line). If the intensities differ from other intensities by a threshold amount, an image artifact is assumed to exist.

Figure 7:
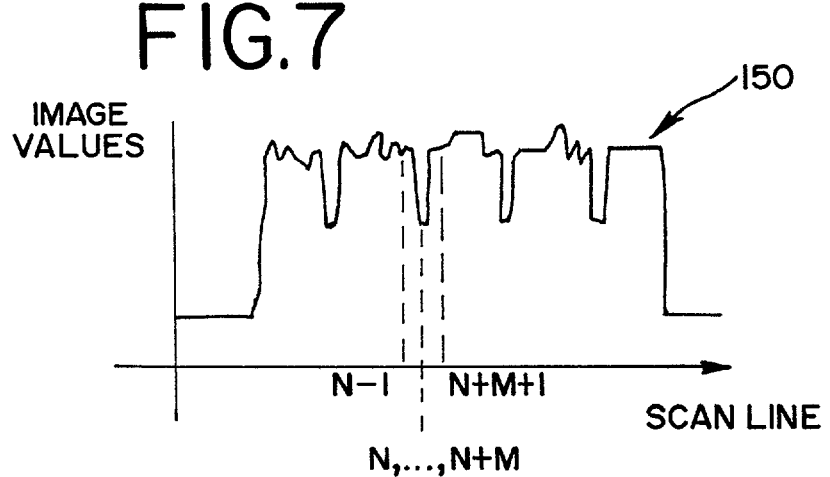
FIG. 7 is a graphical representation of image values as a function of scan line for an azimuthal cross-section of the image of FIG. 6.
Figure 8:
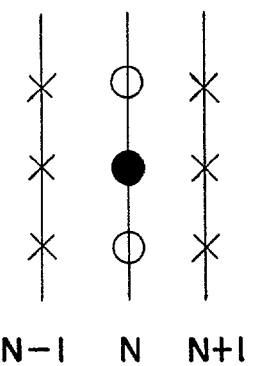
FIG. 8 is a graphical representation of value distribution.

Intensities associated with an image artifact are replaced in act 56. The intensities are replaced by intensities from adjacent samples, groups of samples, or scan lines. In act 56, if the values near the range sample of interest, which has been identified as an artifact sample, are above the threshold, the range sample of interest is replaced with a replacement value. The replacement value may be a spatial and/or temporal average of two or more values from neighboring values in space and/or frame number (i.e., time) and may be inclusive of the current sample value to be replaced. FIGS. 6 and 7 graphically illustrate acts 56 and 57 in FIG. 4. In FIG. 6, the image 100 includes a region 110 with graphically noticeable contrast agent detection. Within the region 110, four lines 120 of reduced sensitivity are shown due to increased collateral destruction pulses. In FIG. 7, an example of the image values as a function of the image scan lines for the azimuthal slice 130 in FIG. 6 is shown. Due to the collateral pulses destroying more agent in the four lines indicated, and, as compared to the other scan lines, the image intensity values are lower. The replacement step is performed for each range sample in act 57 for a scan line associated with image artifacts. For example, an average from all six neighboring values in a single frame from the lines N−1 and N+M+1 can be used to replace a value at line N when M=0. FIG. 8 shows three scan line regions with the Xs indicating immediate neighboring samples, Os indicating the values on the line that has artifacts, and a solid O is the sample to be replaced. In another example, the average includes the value at line N that is replaced with the average value. More or less than the six immediate neighboring values may be used to replace the value of interest. Values used to compute the replacement value may come from other lines in the same frame and/or other values in other frames. Any algorithm may be used to determine the replacement value(s) including replacement by a single value, extrapolation, interpolation or other algorithms.

Another method that may be used to replace samples identified as artifacts is to average samples from other frames where the image values in each frame are generated from a transmit sequence that started on a scan line that was different between frames. Since the location of the artifacts are predictable and are generated within specific groups of transmit pulse firings, a group of transmit firings can be adjusted to start on different scan lines in each unique frame. This effectively shifts the artifacts by a scan line or a few scan lines. This method allows samples from different frames to be used in determining a replacement value(s) without spatial smoothing, reducing the possibility that samples from other frames used to determine a replacement value(s) will be corrupted by artifacts.

The frame may be spatially averaged around and including the sample of interest on line N for the sample at line N before performing act 56 or alternatively act 54. Spatially averaging samples before identifying those that contain artifacts in act 54 can improve the ability of the method to minimize artifacts in the image. Prior temporal averaging may be performed.

If an artifact is identified on more than one line, the values for the plurality of lines may all be replaced with replacement values. The size of the area where an artifact is identified may be defined in many ways, such as applying a threshold as discussed above. The size can be predetermined by the system design, user selected, adaptive based on signal characteristics, based on specific agent types, or other means. The process is repeated for each as represented by act 58.

While the invention has been described above by reference to various embodiments, it will be understood that many changes and modifications can be made without departing from the scope of the invention. For example, transmit pulses sequences of various combinations may be used for providing substantially similar energy sequences along a scan line. Destruction pulses may be transmitted along fewer or more scan lines than imaging pulses.

It is therefore intended that the foregoing detailed description be understood as an illustration of the presently preferred embodiments of the invention, and not as a definition of the invention. It is only the following claims, including all equivalents, which are intended to define the scope of the invention.

What is claimed is:

1. In a method of transmitting a sequence of transmit pulses for scanning a region of a target including contrast agents, the improvement wherein:
   a substantially similar energy sequence is provided for substantially each transmit scan line in the region of at least eight scan lines, where the energy sequence includes at least one collateral energy pulse between two imaging pulses.

2. The method of claim 1 responsive to the transmit pulses characterized by a flow sample interleave ratio that is equal to a flow sample count minus one.

3. The method of claim 1 further comprising energy responsive to a destruction pulse where an image is responsive to the energy of the imaging pulses and substantially free of response to the energy of the destruction pulse.

4. The method of claim 1 responsive to the transmit pulses characterized by a flow sample interleave ratio that is two and a flow sample count that is three.

5. The method of claim 4 comprising e eCeCeCe e where "e" represents a collateral energy pulse and "C" represents an imaging energy pulse.

6. The method of claim 1 responsive to the transmit pulses characterized by a flow sample interleave ratio that is three and a flow sample count that is four.

7. The method of claim 6 comprising e eC eCeeCe Ce e where "e" represents a collateral energy pulse and "C" represents an imaging energy pulse.

8. The method of claim 1 responsive to the transmit pulses characterized by a flow sample interleave ratio that is three and a flow sample count that is three.

9. The method of claim 8 comprising e eC eCe Ce e where "e" represents a collateral energy pulse and "C" represents a imaging energy pulse.

10. The method claim 1 wherein the flow sample interleave ratio is an integer multiple of one less than a flow sample count.

11. A method for imaging contrast agents with an ultrasound system, the method comprising the acts of:
 (a) generating a substantially similar transmit pulse sequence for substantially each line in a scanned region of at least eight scan lines; and
 (b) interleaving collateral pulses from a transmission along a first scan line between at least two imaging pulses along a second different scan line, the transmit pulse sequence including energy from collateral pulses of adjacent scan lines and imaging pulses on each line.

12. The method of claim 11 wherein (b) comprises interleaving with a flow sample interleave ratio that is equal to a flow sample count minus one.

13. The method of claim 11 further comprising:
 (c) transmitting a destruction pulse where an image is responsive to the energy of the imaging pulses and substantially free of response to the energy of the destruction pulse.

14. The method of claim 11 wherein (b) comprises interleaving with a flow sample interleave ratio that is two and a flow sample count that is three.

15. The method of claim 11 wherein (b) comprises interleaving with a flow sample interleave ratio that is three and a flow sample count that is four.

16. The method of claim 11 wherein (b) comprises interleaving with a flow sample interleave ratio that is three and a flow sample count that is three.

17. The method claim 11 wherein (b) comprises interleaving with a flow sample interleave ratio that is an integer multiple of one less than a flow sample count.

18. The method of claim 11 further comprising:
 (c) determining a loss of correlation between the at least two imaging pulses in the sequence along one scan line.

19. The method of claim 11 further comprising:
 (c) determining movement from at least two imaging pulses in the sequence along the second scan line.

20. A method for imaging contrast agents with an ultrasound system, the method comprising the acts of:
 (a) transmitting a first pulse along a first scan line;
 (b) transmitting a second pulse along a second scan line after (a), the second scan line adjacent the first scan line;
 (c) transmitting a third pulse along the first scan line after (b); and
 (d) repeating (a), (b) and (c) for a different set of scan lines such that a substantially same sequence of collateral and imaging pulses is provided for each of a plurality of scan lines including the scan lines of the different sets.

21. The method of claim 20 wherein acts (a) through (c) comprise interleaving with a flow sample interleave ratio that is equal to a flow sample count minus one.

22. The method of claim 21 wherein acts (a) through (c) comprise interleaving with a flow sample interleave ratio that is two and a flow sample count that is three.

23. The method of claim 21 wherein acts (a) through (c) comprise interleaving with a flow sample interleave ratio that is three and a flow sample count that is four.

24. The method of claim 20 wherein acts (a) through (c) comprise interleaving with a flow sample interleave ratio that is three and a flow sample count that is three.

25. The method claim 20 wherein (a) through (c) comprises interleaving with a flow sample interleave ratio that is an integer multiple of one less than a flow sample count.

26. A method for imaging contrast agents with an ultrasound system, the method comprising:
 (a) transmitting pulses with a flow sample interleave ratio greater than one;
 (b) generating a substantially similar imaging pulse and collateral pulse energy sequence for substantially each transmit line in a scanned region including at least eight transmit lines; and
 (c) sampling energy responsive to each transmitted pulse.

27. The method of claim 26 wherein (a) comprises transmitting with a flow sample interleave ratio that is equal to a flow sample count minus one.

28. A method for imaging contrast agent with an ultrasound system, the method comprising the acts of:
 (a) transmitting acoustic energy along first and second lines in a target including contrast agent;
 (b) obtaining signals representing the first and second lines in response to (a) and the contrast agent;
 (c) determining intensities associated with the signals;
 (d) comparing the intensities associated with the first line to a value; and
 (e) replacing the signals for the first line as a function of the signals of the second line in response to (d).

29. The method of claim 28 wherein (e) comprises replacing the signals associated with the first scan line with the signals associated with the second scan line.

30. The method of claim 28 wherein (e) comprises interpolating from at least signals associated with the second scan line.

31. The method of claim 28 wherein (e) comprises averaging signals including signals associated with the second scan line.

32. The method of claim 31 wherein the first scan line is adjacent the second scan line.

33. A method for imaging contrast agents with an ultrasound system, the method comprising the acts of:
 (a) identifying first signals associated with an image artifact where the first signals are responsive to contrast agent; and
 (b) replacing the first signals as a function of second signals responsive to the contrast agent.

34. The method of claim 33 wherein (b) comprises replacing the first signals with the second signals, the first signals associated with a first scan line and the second signals associated with a second scan line.

35. The method of claim 33 wherein (b) comprises interpolating the second signals from third and fourth signals, the third and fourth signals associated with scan lines adjacent to a scan line corresponding to the first signals.

36. The method of claim 33 wherein (b) comprises averaging signals including the second signals.

37. The method of claim 36 wherein the first signals correspond to a first scan line adjacent to a second scan line corresponding the second signals.

* * * * *